United States Patent [19]

Itoh et al.

[11] Patent Number: 4,579,822

[45] Date of Patent: Apr. 1, 1986

[54] PROCESS FOR PRODUCING DIHYDROXYACETONE KINASE

[75] Inventors: Nobuya Itoh, Suzuka; Kuniyoshi Matsunaga, Ichinomiya, both of Japan

[73] Assignee: Amano Pharmaceutical Co., Ltd., Nagoya, Japan

[21] Appl. No.: 598,746

[22] Filed: Apr. 10, 1984

[30] Foreign Application Priority Data

Apr. 16, 1983 [JP] Japan .................................. 58-67627

[51] Int. Cl.$^4$ ......................... C12N 9/12; C12Q 1/48; C12R 1/645
[52] U.S. Cl. ..................................... 435/194; 435/15; 435/911
[58] Field of Search ................................. 435/194, 15

[56] References Cited

PUBLICATIONS

Lerner et al., Plant Physiology 1977, vol. 59, pp. 15-17.
John W. May et al., Glycerol Utilization by *Schizosaccharomyces Pombe,* J. Gen. Microbiol. 123, 183-185 and 128, 1763-1766 (1981).
K. M. Hofmann, Dihydroxyacetone Kinase of Methanol-Assimilating Yeasts, Zeitschr. Allg. Mikrobiol. 21 (3) 219-224 (1981).

*Primary Examiner*—Lionel M. Shapiro
*Attorney, Agent, or Firm*—Wegner & Bretschneider

[57] ABSTRACT

A process for producing dihydroxyacetone kinase comprises the cultivation of the DHAK-producing strains of genus Schizosaccharomyces, and the purification of dihydroxyacetone kinase from the culture.

1 Claim, 5 Drawing Figures

PROCESS FOR PRODUCING DIHYDROXYACETONE KINASE

BACKGROUND OF THE INVENTION

1. Field of the Invention

The present invention relates to a process for producing dihydroxyacetone kinase (referred to as DHAK) which is formed by strains of genus Schizosaccharomyces.

2. Decription of the Prior Art

DHAK is an enzyme which catalyzes the reaction of transferring the phosphate group of a phosphate donor to dihydroxyacetone (referred to as DHA) to form dihydroxyacetone phosphate. The equation of the reaction where adenosine triphosphate (referred to as ATP) is used as the phosphate donor is as follows:

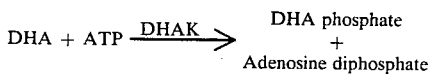

DHA + ATP $\xrightarrow{\text{DHAK}}$ DHA phosphate + Adenosine diphosphate

The present inventors made extensive studies of the glycerol determination methods employing glycerol dehydrogenase. However, since the reaction catalyzed by glycerol dehydrogenase is reversible as given by the following equation, there has been a disadvantage such that, in order to promote the forward reaction, it is required to add excess nicotinamide adenine dinucleotide (referred to as NAD+) to the reaction mixture or conduct the reaction in as high a pH region as from 10 to 11.

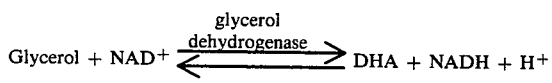

Glycerol + NAD+ $\underset{\text{dehydrogenase}}{\overset{\text{glycerol}}{\rightleftarrows}}$ DHA + NADH + H+

For the purpose of promoting the forward reaction, it is desired to exclude the formed DHA from of the reaction system. Thus, the present inventors examined various enzymes suitable for the purpose, and found DHAK to be effective.

DHAK are known to occur in, for example, *Candida methylica* [Z. Allg. Mikrobiol., 20, 389 (1980); ibid., 21, 219 (1981)], *Gluconobacter suboxidans* (Joint Technical Meeting held by the Chubu Branch and the Kansai Branch of the Agricultural Chemical Society of Japan, Oct. 9, 1981, Abstract of the Lectures, p.3), *Acetobacter xylinum* (J. Bacteriol., 127, 747 (1976)), and Dunaliella, a green alga, (Plant Physiol., 59, 15 (1977)) and Biochim. Biophys. Acta, 615, 1 (1980)). However, these strains are unsatisfactory in the low productivity, the lack of enzyme stability, and the difficulty to obtain the highly purified enzyme preparation, etc.

SUMMARY OF THE INVENTION

An object of the invention is to provide a fermentation process for producing DHAK excellent in properties and useful for enzymatic determination of glycerol.

Another object of the invention is to provide a fermentation process for producing highly pure DHAK in a high yield.

According to the present invention, there is provided a process for producing DHAK, which comprises the cultivation of a DHAK-producing strain of genus Schizosaccharomyces, and the purification of DHAK from the culture.

DESCRIPTION OF THE PREFERRED EMBODIMENTS

Figure 2:
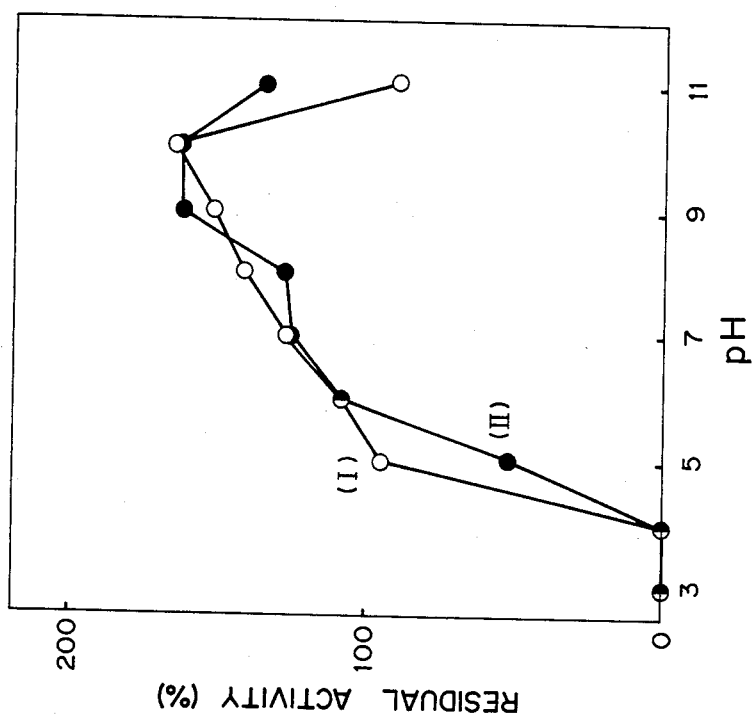
FIG. 2 shows the effect of pH on the stabilities of DHAK (I) and DHAK (II).

Triokinase (EC 2.7.1.28), which catalyzes the same reaction of DHAK, has been known to exist in guinea pig liver, rat liver, and *Bacillus subtilis* [Meth. Enzymol., 5, 362 (1962), Eur. J. Biochem., 31, 59 (1972), and The Enzymes, 2nd, ed., 6, 75 (1962)]. DHAKs produced from genus Schizosaccharomyces and the DHAK reported previously are regarded to be different from triokinase in that these DHAKs exhibit low activity toward DL-glyceraldehyde whereas triokinase catalyzes the phosphorylations of DHA and DL-glyceraldehyde at nearly the same rate.

The microorganism used in the process according to the invention may be any strain belonging to the genus Schizosaccharomyces which has an ability to produce DHAK; for example, available strains include *Schizosaccharomyces pombe* IFO 0340, *S. pombe* IFO 0354, *S. malidevorans* IFO 1608, *S. japonicus* IFO 1609, and *S. octosporus* IAM 12257. Among these, *S. pombe* IFO 0354 is preferred for its high productivity. All the strains above-mentioned have been deposited in recognized depositories respectively, the abbreviated mark of "IFO" therein representing Institute for Fermentation, Osaka, Japan, and "IAM" representing Institute of Applied Microbiology, University of Tokyo, Japan.

Any synthetic or natural medium containing a carbon source, a nitrogen source, and inorganic compounds may be used as the nutrient medium for cultivating the above strains. Glucose, fructose, maltose or sucrose is suitable for the carbon source and malt extract, peptone, yeast extract or meat extract, is used for the nitrogen source. Salts of metals such as potassium, sodium, magnesium, iron, etc. are used for the inorganic compounds. The cultivation is preferably carried out at a temperature of 25°–35° C. The pH of the medium is in the range of from 5 to 7. The cultivation is carried out for 24–72 hours so that the maximum enzyme activity is attained.

After cultivation, the cells are harvested by centrifugation or filtration. Then, the cells are disrupted with a Dyno Mill KDL or a French press, or a treatment with an organic solvent such as acetone or a lytic enzyme. The cell debris is removed by centrifugation or filtration. Thereafter, the DHAK is purified from the cell-free extract by means of conventional techniques such as precipitation with an organic solvent, sodium sulfate or ammonium sulfate, adsorption chromatography, ion exchange chromatography, gel filtration, etc.

The standard assay mixture for measuring the activity of DHAK consists of 1.0 ml of 0.1M triethanolamine-HCl buffer (pH 7.5), 2.5 mM ATP, 4 mM MgSO4, 0.2 mM NADH, 1.0 mM DHA, 2.5 units of glycerol-3-phosphate dehydrogenase (Boehringer Mannheim GmbH), and 0.01 ml of enzyme solution. The reaction is started by adding enzyme solution, and the decrease of the absorbance at 340 nm is measured spectrophotometrically at 25° C. In the blank assay, DHA is excluded from the reaction mixture. One unit of the enzyme activity is defined as the amount of enzyme which catalyzes the formation of 1 μmol NAD+ in one minute under the above conditions. The above reaction is represented by the following equations:

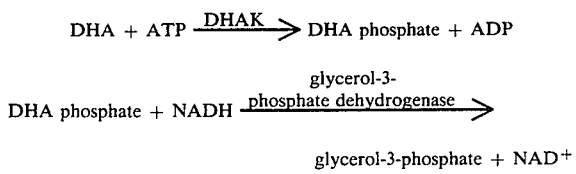

$$\text{DHA} + \text{ATP} \xrightarrow{\text{DHAK}} \text{DHA phosphate} + \text{ADP}$$

$$\text{DHA phosphate} + \text{NADH} \xrightarrow{\text{glycerol-3-phosphate dehydrogenase}} \text{glycerol-3-phosphate} + \text{NAD}^+$$

DHAK of *Schizosaccharomyces pombe* IFO 0354, as will be described in the following examples, comprises two isoenzymes, one being found in the fractions eluted with an about 0.12M KCl solution (this isoenzyme is referred to as DHAK (I)) and the other in the fractions eluted with an about 0.16M KCl solution (this isoenzyme is referred to as DHAK (I)) with a DEAE-Sepharose column chromatography. Thereafter, DHAK (I) and DHAK (II) are independently purified. The properties of DHAK (I) and DHAK (II) obtained from *Schizosaccharomyces pombe* IFO 0354 are described below.

(1) Reaction catalyzed by the enzyme

The enzymes (DHAK (I) and DHAK (II)) catalyze the reaction of transferring the phosphate group of a phosphate donor such as ATP to DHA to form dihydroxyacetone phosphate.

(2) Substrate specificity of the enzyme

The reaction mixture for measuring the substrate specificity of DHAK consists of 1.0 ml of 0.1M triethanolamine-HCl buffer (pH 7.5), 2.5 mM ATP, 4 mM MgSO4, 0.2 mM NADH, 1.3 mM phosphoenolpyruvate, 6 units of pyruvate kinase, 6 units of lactate dehydrogenase (Boehringer Mannheim GmbH), 0.01 ml of enzyme solution and each substrate (1.0 mM) as shown in Table 1. The reaction is started by adding enzyme solution and measured the decrease in the absorbance at 340 nm at 25° C. The above reaction is represented by the following equations:

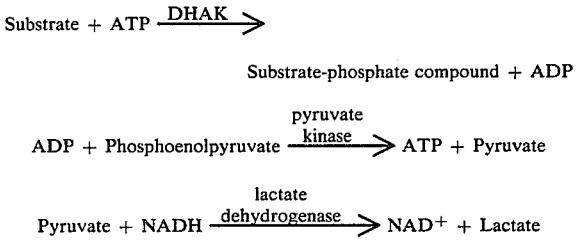

$$\text{Substrate} + \text{ATP} \xrightarrow{\text{DHAK}} \text{Substrate-phosphate compound} + \text{ADP}$$

$$\text{ADP} + \text{Phosphoenolpyruvate} \xrightarrow{\text{pyruvate kinase}} \text{ATP} + \text{Pyruvate}$$

$$\text{Pyruvate} + \text{NADH} \xrightarrow{\text{lactate dehydrogenase}} \text{NAD}^+ + \text{Lactate}$$

As shown in Table 1, DHAK (I) and DHAK (II) act on DHA, but slightly on DL-glyceraldehyde, and not on the other substrates examined here.

TABLE 1

| Substrate | Relative activity | |
|---|---|---|
| | DHAK (I) | DHAK (II) |
| DHA | 100% | 100% |
| DL-Glyceraldehyde | 27 | 12 |
| Glycerol | 0 | 0 |

TABLE 1-continued

| Substrate | Relative activity | |
|---|---|---|
| | DHAK (I) | DHAK (II) |
| 1,2-Propanediol | 0 | 0 |
| 1,3-Propanediol | 0 | 0 |
| Acetol | 0 | 0 |
| Acetoin | 0 | 0 |
| Glycerol-3-phosphate | 0 | 0 |
| DL-Glyceric acid | 0 | 0 |

(3) Specificity of the enzyme for phosphate donor

As shown in Table 2, ATP is best phosphate donor for both DHAK (I) and DHAK (II).

TABLE 2

| Phosphate donor | Relative activity | |
|---|---|---|
| | DHAK (I) | DHAK (II) |
| Adenosine 5'-triphosphate | 100% | 100% |
| Uridine 5'-triphosphate | 3.9 | 3.6 |
| Inosine 5'-triphosphate | 0 | 0 |
| Cytidine 5'-triphosphate | 0 | 0 |
| Guanosine 5'-triphosphate | 0 | 0 |

(4) Specificity of the enzyme for divalent metal cations

Each divalent metal cation (4 mM) was added to the reaction mixture and the activity of the enzyme was measured. The results show that DHAK (I) and DHAK (II) exhibit no enzyme activity in the absence of divalent metal cations. DHAK (I) exhibits the maximum activity in the presence of $Ca^{2+}$ and DHAK (II) in the presence of $Mg^{2+}$ (Table 3).

TABLE 3

| Metal cation | Relative activity | |
|---|---|---|
| | DHAK (I) | DHAK (II) |
| None | 0% | 0% |
| MgSO4 | 100 | 100 |
| CaCl2 | 125 | 44 |
| CoCl2 | 29 | 22 |
| MnCl2 | 15 | 9 |
| NiCl2 | 0 | 0 |

(5) Optimum pH for the enzyme activity

Figure 1:
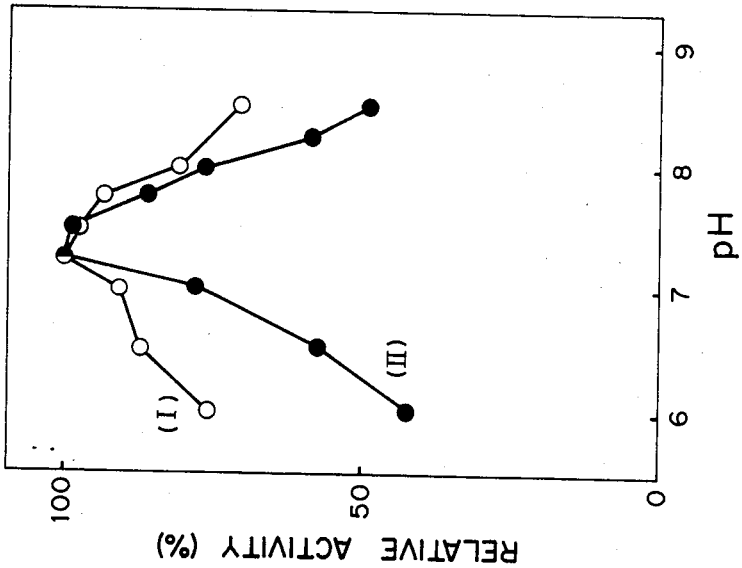
FIG. 1 shows the optimum pHs of the DHAK (I) and DHAK (II) prepared from *Schizosaccharomyces pombe* IFO 0354 according to the process of the invention.

The enzyme activities of DHAK (I) and DHAK (II) were measured at various pHs. The results show that the optimum pHs of DHAK (I) and DHAK (II) are around 7.3 (FIG. 1).

(6) pH Stability of the enzyme

Residual activities of DHAK (I) and DHAK (II) were measured after incubation for 2 hours at 25° C. at various pHs. The results show that DHAK (I) is stable in a pH range of from 5 to 11, and DHAK (II) from 6 to 11 (FIG. 2).

(7) Optimum temperature for the enzyme activity

The activities of DHAK (I) and DHAK (II) were measured at various temperatures at pH 7.0. DHAK (I) shows the maximum activity at about 60° C. and DHAK (II) at about 55° C.

(8) Thermal stability of the enzyme

Figure 4:
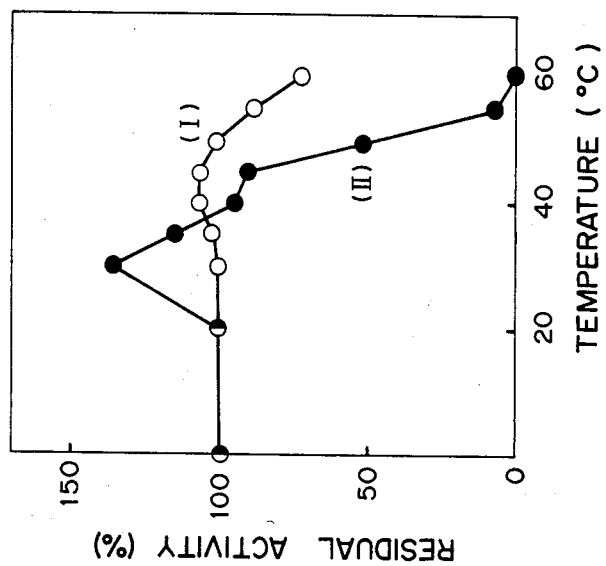
FIG. 4 shows the effect of temperature on the stabilities of DHAK (I) and DHAK (II).
Figure 3:
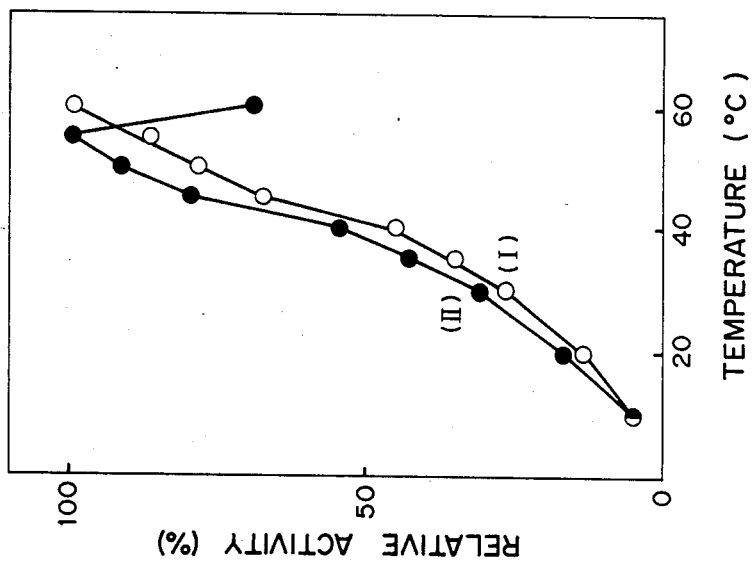
FIG. 3 shows the optimum temperatures for DHAK (I) and DHAK (II).

Residual activities of DHAK (I) and DHAK (II) were measured after incubation for 15 minutes at pH 7.0. The results indicate that DHAK (I) is stable below 50° C. and DHAK (II) below 40° C. (FIG. 4).

(9) Km values of the enzyme for various substrates and coenzyme

Michaelis constants (Km values) of DHAK (I) and DHAK (II) for DHA, DL-glyceraldehyde and ATP under the conditions of at pH 7.5 and at 25° C. are as follows:

DHAK (I): $8.4 \times 10^{-6}$M, $2.1 \times 10^{-5}$M, $2.2 \times 10^{-4}$M
(DHAK (II): $2.0 \times 10^{-5}$M, $3.2 \times 10^{-5}$M, $9.1 \times 10^{-4}$M As regards the effect of $Mg^{2+}$ concentration in the reaction mixture, both DHAK (I) and DHAK (II) exhibit the sufficient activities at 4 mM or above.

(10) Molecular weight of the enzyme

Molecular weights of DHAK (I) and DHAK (II), as measured by gel filtration method with Sephadex G-200 (Pharmacia Fine Chemicals Co.), were both calculated to be about 145,000.

Application of the DHAK (I) or DHAK (II) to the glycerol assay system employing glycerol dehydrogenase has enabled higher sensitive determination of glycerol. This assay system is also used for the determination of triglyceride employing lipase and glycerol dehydrogenase. In addition, the enzymes are expected to be widely used for determinations of dihydroxyacetone and ATP and for the enzymatic production of dihydroxyacetone phosphate.

The invention is illustrated in more detail referring to the following test example and preparation examples.

TEST EXAMPLE (Tests for DHAK-producing ability of various strains)

Each strain of the genus Schizosaccharomyces shown in Table 4 was inoculated to 100 ml of a medium (pH6.2) in a 500-ml shaking flask. The composition of the medium was as follows: malt extract 1%, peptone 0.3%, yeast extract 0.1%, $K_2HPO_4$ 0.2%, $MgSO_4.7H_2O$ 0.05%, KCl 0.05%, $FeSO_4.7H_2O$ 0.001%. The cultivation was carried out at 30° C. for 48 hours with shaking. The cells of each strain were collected by centrifugation, washed with 30 ml of a 20 mM Tris-Hcl buffer (pH 7.0), disrupted in a mortar with aluminum oxide, and extracted with 5 ml of the same buffer. The extract was centrifuged (10,000 rpm) for 10 min. The enzyme activity of the cell-free extract thus obtained was measured. Results of the test are as shown in Table 4.

TABLE 4

| Strain | Activity (units/dl medium) |
| --- | --- |
| Schizosaccharomyces pombe IFO 0340 | 0.7 |
| S. pombe IFO 0354 | 14.0 |
| S. malidevorans IFO 1608 | 1.2 |
| S. japonicus IFO 1609 | 0.2 |
| S. octosporus IAM 12257 | 4.0 |

EXAMPLE 1

S.pombe IFO 0354 was inoculated from a stocked culture to 100 ml of a medium (pH 6.2) in a 500-ml shaking flask. The composition of the medium was as follows: malt extract 1%, peptone 0.3%, yeast extract 0.1%, $K_2HPO_4$ 0.2%, $MgSO_4.7H_2O$ 0.05%, KCl 0.05%, $FeSO_4.7H_2O$ 0.001%. The cultivation was carried out at 30° C. for 48 hours with shaking. Then, the culture broth was transferred to 10 l of a medium of the same composition as the above in a 20-l jar fermentor and cultured at 30° C. for 48 hours with constant aeration and agitation.

Figure 5:
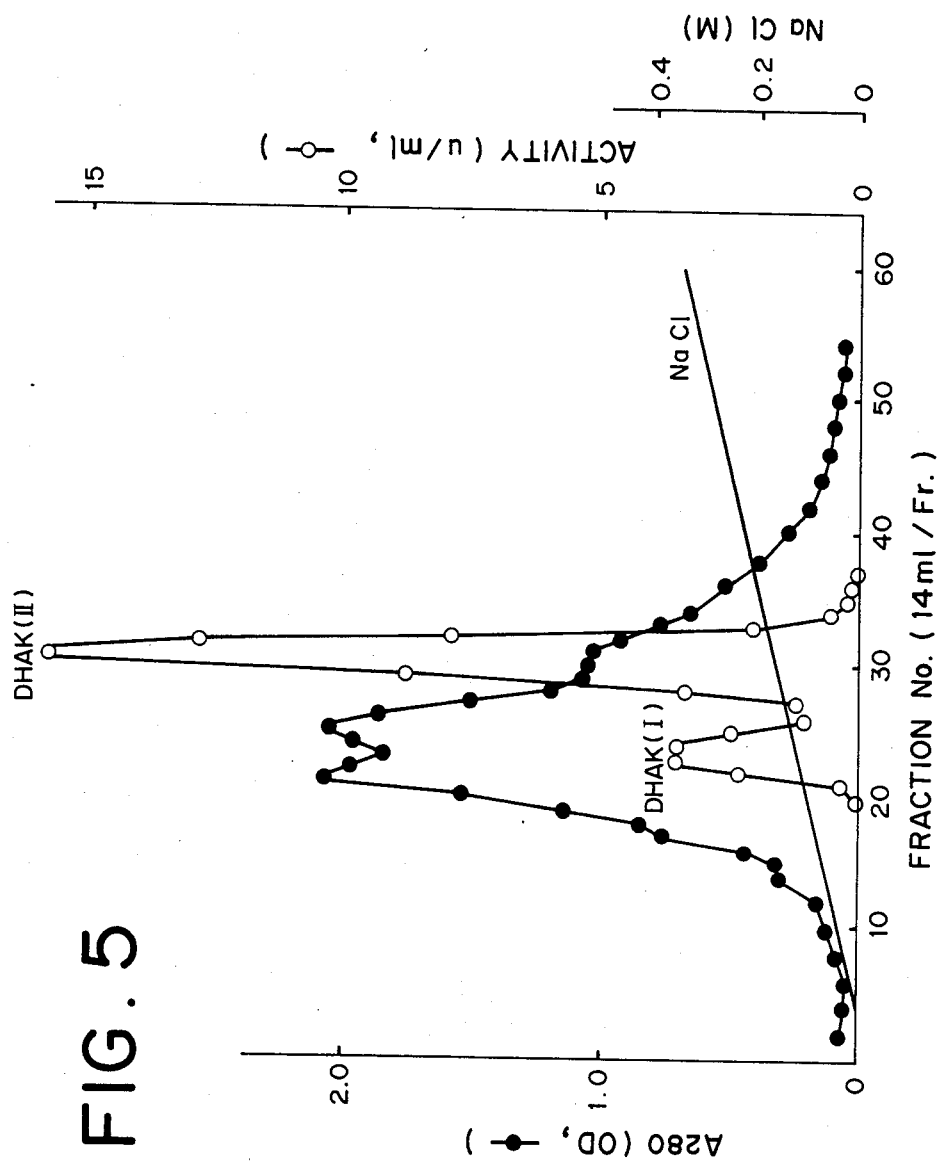
FIG. 5 shows an elution pattern with a DEAE-Sepharose column chromatography of DHAK (I) and DHAK (II).

The cells were collected by centrifugation, suspended in a 20 mM Tris-HCl buffer (pH 7.0), and disrupted for about 10 minutes with a Dyno Mill KDL. The extract was centrifuged to remove the cell debris. A polyethyleneimine solution was added to the resulting supernatant up to the concentration of 0.02%, and the precipitate was removed by centrifugation. The resulting supernatant was then salted out with 40% of ammonium sulfate, and a precipitate was removed. The supernatant was brought to 70% of ammonium sulfate, and the precipitate was collected by centrifugation. The precipitate was dissolved in the same buffer, then subjected to a Sephadex G-25 (Pharmacia Fine Chemicals Co.) column chromatography for desalting. The enzyme solution was applied to a DEAE-Sepharose (Pharmacia Fine Chemicals Co.) column previously equilibrated with the same buffer. After washing the column, the enzyme was eluted with a linear gradient of KCl from 0 to 0.3M. Two peaks of DHAK activity were observed with DEAE-Sepharose column chromatography as shown in FIG. 5. The fractions eluted with 0.12M of KCl (referred to as DHAK (I)) and the fractions eluted with 0.16M KCl (referred to as DHAK (II)) were independently collected.

DHAK (I) and (II) were precipitated by adding ammonium sulfate to the combined fractions up to 80% saturation, respectively. Each enzyme precipitate was collected by centrifugation, dissolved in the same buffer, and desalted with Sephadex G-25 column chromatography. Each resulting enzyme solution was passed through a Blue-Sepharose (Pharmacia Fine Chemicals, Co.) column previously equilibrated with a 40 mM Tris-HCl buffer (pH 7.0), and active fractions were concentrated by ultrafiltration. Thus, 120 units of DHAK (I) and 360 units of DHAK (II) were obtained.

PREPARATION OF EXAMPLE 2

In the same manner as in Example 1 by using S. octosporus IAM 12257, 50 units of DHAK was obtained.

What is claimed is:

1. Process for producing dihydroxyacetone kinase, which comprises cultivation of Schizosaccharomyces pombe strain IFO 0354 and purification of dihydroxyacetone kinase extrated from the culture.

* * * * *